(12) United States Patent
Onuma

(10) Patent No.: US 9,989,494 B2
(45) Date of Patent: Jun. 5, 2018

(54) METHOD FOR MANUFACTURING CHIP COMPRISING MICROCHANNEL AND CHIP

(71) Applicant: ARKRAY, INC., Kyoto (JP)

(72) Inventor: Naotsugu Onuma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 483 days.

(21) Appl. No.: 14/621,702

(22) Filed: Feb. 13, 2015

(65) Prior Publication Data
US 2015/0233865 A1    Aug. 20, 2015

(30) Foreign Application Priority Data

Feb. 14, 2014  (JP) .................................. 2014-026816
Feb. 6, 2015   (JP) .................................. 2015-022461

(51) Int. Cl.
*G01N 27/447* (2006.01)
*B32B 38/00* (2006.01)
*B32B 37/12* (2006.01)
*B01L 3/00* (2006.01)

(52) U.S. Cl.
CPC .. *G01N 27/44791* (2013.01); *B01L 3/502707* (2013.01); *B32B 37/12* (2013.01); *B32B 38/0008* (2013.01); *B01L 2300/16* (2013.01)

(58) Field of Classification Search
CPC ....... A61B 5/14; A61B 5/1405; B01L 3/5027; B01L 3/502707; B01L 3/502746; B01L 2300/16; B01L 2300/161; B01L 2300/165; G01N 2030/567
See application file for complete search history.

(56) References Cited

U.S. PATENT DOCUMENTS

| | | | |
|---|---|---|---|
| 4,920,176 A | 4/1990 | Jorgensen, Jr. | |
| 6,355,198 B1 | 3/2002 | Kim et al. | |
| 8,394,336 B2 * | 3/2013 | Curcio | G01N 33/558 422/400 |
| 2007/0199821 A1 * | 8/2007 | Chow | G01N 27/44795 204/451 |
| 2008/0044830 A1 | 2/2008 | Tovar et al. | |
| 2010/0101953 A1 | 4/2010 | Yokoyama et al. | |
| 2010/0175996 A1 | 7/2010 | Tanaka et al. | |
| 2012/0138461 A1 | 6/2012 | Sugiyama et al. | |
| 2013/0309778 A1 * | 11/2013 | Lowe | B01L 3/502715 436/501 |

FOREIGN PATENT DOCUMENTS

| | | |
|---|---|---|
| EP | 2278331 A1 | 1/2011 |
| JP | H02-269137 A | 11/1990 |
| JP | 2005-249572 A | 9/2005 |
| JP | 2008-019348 A | 1/2008 |
| JP | 2008-525763 A | 7/2008 |

(Continued)

OTHER PUBLICATIONS

Extended European Search Report issued in corresponding European Patent Application No. 15154707.2 dated Jul. 24, 2015.

(Continued)

*Primary Examiner* — Alexander S Noguerola
(74) *Attorney, Agent, or Firm* — Morgan, Lewis & Bockius LLP

(57) ABSTRACT

A method for manufacturing a chip that includes a microchannel is described, wherein the method includes the steps of: fixing a cationic polymer having a quaternary onium group to at least one surface of each of a pair of resin substrates; and joining the resin substrates together on the surfaces on which the cationic polymer has been fixed.

6 Claims, 5 Drawing Sheets

(56) References Cited

FOREIGN PATENT DOCUMENTS

| JP | 2009-084463 A | 4/2009 | |
| JP | 2009-145245 A | 7/2009 | |
| JP | 2012-132894 A | 7/2012 | |
| WO | 03/055611 A1 | 7/2003 | |
| WO | 2007/090779 A1 | 8/2007 | |
| WO | 2008/029684 A1 | 3/2008 | |
| WO | WO 2012 050809 A1 * | 4/2012 | ............... B05D 5/00 |

OTHER PUBLICATIONS

Office Action issued in corresponding Chinese Patent Application No. 201510082773.3 dated Dec. 16, 2016 (partial English translation).

Qun, "Construction of Functional Polymer Surface and Application thereof to Life Analysis," Chinese Doctoral Dissertations Full-Text Database, Engineering Science and Technology I, B014-B022 (2014) (partial English translation).

Office Action issued in corresponding Japanese Patent Application No. 2015-022461 dated Jan. 26, 2016.

Office Action issued in corresponding European Patent Application No. 15154707.2 dated Jul. 4, 2016.

Extended European Search Report issued in corresponding European Patent Application No. 17181689.5 dated Nov. 14, 2017.

Office Action issued in corresponding Chinese Patent Application No. 201510082773.3 dated Aug. 17, 2017 (partial English translation).

Chang Liu, PDMS Microfluidic Channel, p. 351 (2012) (partial English translation).

* cited by examiner

METHOD FOR MANUFACTURING CHIP COMPRISING MICROCHANNEL AND CHIP

BACKGROUND OF THE INVENTION

1. Field of the Invention

The present disclosure relates to a chip comprising a microchannel and a method for manufacturing the same.

2. Description of Related Art

Glass is an example of a typical material used for capillary electrophoresis or microchannel electrophoresis. However, a capillary or microchannel chip formed of glass has not been used widely in the field of clinical laboratory testing, since such a chip is expensive and requires complex processes, chemical modifications, and careful handling, for example. For solving these problems, there have been attempts to manufacture microchannel chips of resin. In general, the microchannel chip is formed by preparing a resin part provided with a micro-structure on its surface and joining the resin part with another resin part that serves as a covering. However, the conventional joining method that uses adhesives or heat sealing may cause problems. For example, the microchannel may be buried/covered or deformed.

JP 2008-19348 describes a method (Method-1) of irradiating resin surfaces with ultraviolet rays and heat-pressing the irradiated surfaces together. The document describes further a method (Method-2) of irradiating the resin surfaces with ultraviolet rays and then treating with a silane coupling agent so as to heat-press the treated surfaces together. JP 2005-249572 describes a method (Method-3) of forming a polymer film after masking the surfaces to be joined except for the micro-structure and then detaching the masking for joining the surfaces. JP 2009-145245 describes a method (Method-4) of forming in advance a microchannel and then fixing a cationic functional group to an inner wall of the channel. JP 2012-132894 describes a method (Method-5) of joining resins by a covalent bond via a crosslinking agent so as to expose a cationic functional group of the crosslinking agent on a microchannel surface.

SUMMARY OF THE INVENTION

However, Methods 1-5 as described in these patent applications raise problems as described below. Specifically, in Method-1, the inner wall of the formed microchannel does not have any positive electric charge. In Method-2, it is impossible to complete dehydration of silanol in a short time and within a durable temperature range for the resin, and thus it is difficult to maintain the stability of the charge state of the microchannel inner wall. In Method-3, there is a necessity of separately conducting a precise masking and further conducting an operation of removing the masking before a joining step, rendering the manufacturing method arduous. In Method-4, it is required to repeatedly feed a coating liquid to a microchannel that has been formed and to dry the microchannel, rendering the operations arduous. In Method-5, the resulting microchannel does not provide a sufficient level of accuracy for hemoglobin analysis.

In a capillary electrophoresis, the charge state of the microchannel inner wall is the key. Namely, the charge state has a significant influence on the time period required for the analysis and on the separation state. Therefore, with the foregoing in mind, it is an object of the present disclosure to provide a simple method for manufacturing a chip comprising a microchannel, which reduces deformation of a channel during manufacturing of the chip and which allows introduction of a positive electric charge into the inner wall of the microchannel.

In one or a plurality of embodiments, the present disclosure relates to a method for manufacturing a chip comprising a microchannel, the method comprising: fixing a cationic polymer having a quaternary onium group on at least one surface of each of a pair of resin substrates; and joining the resin substrates together on the surfaces on which the cationic polymer has been fixed.

In one or a plurality of embodiments, the present disclosure relates to a method for manufacturing a chip comprising a microchannel, the method comprising: subjecting at least one surface of each of a pair of resin substrates to either a gas phase surface treatment or a liquid phase surface treatment; bringing a cationic polymer solution having a quaternary onium group into contact with the treated surfaces; and joining the resin substrates together on the surfaces that has been brought into contact with the cationic polymer solution.

In one or a plurality of embodiments, the present disclosure relates to a chip comprising a microchannel, which is manufactured by the manufacturing method of the present disclosure.

According to the present disclosure, it is possible to provide a method for manufacturing a chip, where the method is simple, and enabling to reduce deformation of the channel during manufacturing the chip and to introduce positive electric charge into the inner wall of the microchannel.

DETAILED DESCRIPTION OF THE INVENTION

Figure 1A:
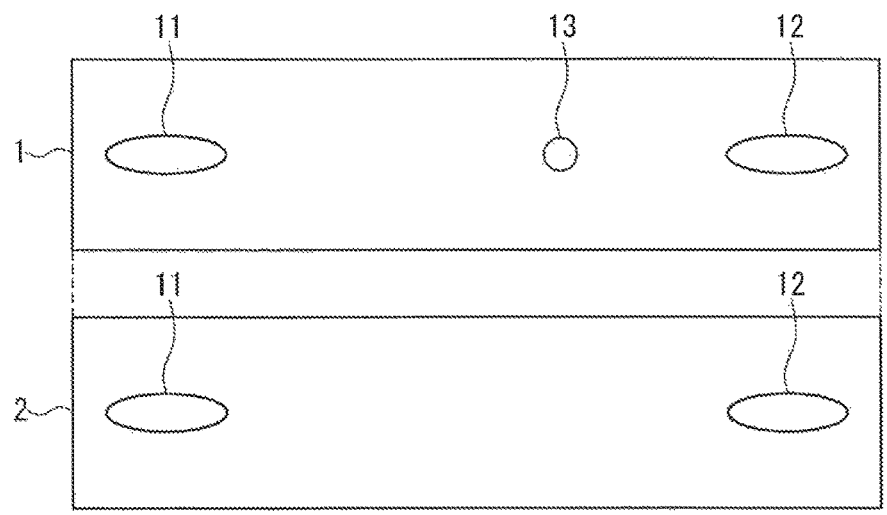
FIGS. 1A, 1B and 1C are schematic diagrams for explaining a microchannel chip of the present disclosure.

The present disclosure is based on a finding that deformation of a microchannel during manufacturing a chip can be reduced and positive electric charge can be introduced efficiently into the microchannel inner wall, by fixing a cationic polymer having a quaternary onium group on resin substrates and by joining the resin substrates together on the surfaces on which the polymer has been fixed. The present disclosure is based on a finding that the respective fractions of hemoglobin can be separated with high accuracy in a short time by using the microchannel chip manufactured by the above-mentioned manufacturing method. The present disclosure is based on a finding that the respective fractions of hemoglobin can be separated with high accuracy in a short time by fixing a cationic polymer having a quaternary onium group to an inner wall of a microchannel, thereby an excellent reproducibility of separation is provided.

The mechanism for separating with high accuracy the respective fractions of hemoglobin in a short time by use of the chip obtained in the manufacturing method of the present disclosure has not been clarified, but it can be assumed as follows. Namely, since a fixed cationic polymer forms a layer three-dimensionally on the channel surface, it applies positive electric charge not only in the vicinity of the channel surface but three-dimensionally in the periphery of the channel surface. Thereby, an electrophoresis running buffer can flow into the space between the upper part of the formed layer and the vicinity of the channel surface. As a result, the EOF (electroosmotic flow) is speeded up, the separation rate is improved and at the same time, the separation accuracy is improved. It is also considered that since the three-dimensional positive electric charge is retained for a long time by the cationic polymer having a quaternary onium group, an excellent reproducibility of separation is provided. However, there is no necessity of interpreting the present disclosure with limitation to these mechanisms.

[Method for Manufacturing Chip]

In one or a plurality of embodiments, the present disclosure relates to a method for manufacturing a chip provided with a microchannel. In one or a plurality of embodiments, the manufacturing method of the present disclosure comprises: fixing a cationic polymer having a quaternary onium group on at least one surface of each of a pair of resin substrates; and joining the resin substrates together on the surfaces on which the cationic polymer has been fixed. In one or a plurality of embodiments, the manufacturing method of the present disclosure includes: subjecting at least one surface of each of a pair of resin substrates to either a gas phase surface treatment or a liquid phase surface treatment; bringing a cationic polymer solution having a quaternary onium group into contact with the treated surfaces; and joining the resin substrates together on the surfaces that has been brought into contact with the cationic polymer solution.

In one or a plurality of embodiments, the manufacturing method of the present disclosure can provide an effect of reducing deformation in the shape of the microchannel. In one or a plurality of embodiments, the manufacturing method of the present disclosure can provide an effect of allowing to introduce sufficient positive electric charge into the inner wall of the microchannel. In one or a plurality of embodiments, the manufacturing method of the present disclosure can provide an effect of allowing to fix a cationic polymer that has a quaternary onium group exhibiting a strong cationic property to the inner wall of the microchannel, in a simple manner.

In one or a plurality of embodiments, the manufacturing method of the present disclosure includes introducing an anionic functional group into at least one surface of a resin substrate. In one or a plurality of embodiments, the anionic functional group can be introduced by conducting either a gas phase surface treatment or a liquid phase surface treatment. In one or a plurality of embodiments, the manufacturing method of the present disclosure includes subjecting at least one surface of the resin substrate to either a gas phase surface treatment or a liquid phase surface treatment. In one or a plurality of embodiments, examples of the anionic functional group include a carboxylic acid group, a sulfonic acid group, a sulfate group, a phosphate group, a phosphonic acid group, a hydroxyl group, and a silanol group. From the viewpoint of ease of introduction, a carboxylic acid group is preferred. In one or a plurality of embodiments, examples of the gas phase surface treatment include a vacuum ultraviolet treatment, a plasma treatment, a corona discharge treatment, a flame treatment, and an ozone treatment. In one or a plurality of embodiments, an example of the liquid phase surface treatment is an alkaline solution treatment.

In one or a plurality of embodiments, the manufacturing method of the present disclosure includes fixation of a cationic polymer having a quaternary onium group on at least one surface of each of a pair of resin substrates. Preferably in one or a plurality of embodiments, the cationic polymer is fixed to a surface into which the anionic functional group has been introduced. In this aspect, the anionic functional group introduced into the resin substrate surface and the quaternary onium group of the cationic polymer are bonded by an ionic bond and the cationic polymer is fixed more strongly to the surfaces of the resin substrates. In one or a plurality of embodiments, the cationic polymer can be fixed by bringing a cationic polymer solution into contact with the surface of the resin substrate to be treated. In one or a plurality of embodiments, examples of the contact include application, immersion, dropping, and spraying.

In one or a plurality of embodiments, the cationic polymer has a quaternary onium group so that it exhibits a strong cationic property and improves the separation accuracy of the chip. In one or a plurality of embodiments, the "onium group" in the present disclosure refers to a functional group composed of a cationic salt having a number of bonds greater by one than the standard number of bonds. In one or a plurality of embodiments, the "onium group" in the present disclosure includes a cation generated by coordinating H+ or a cationic atomic group R+ in a compound including an element having an unshared electron pair. In one or a plurality of embodiments, examples of the quaternary onium group include a quaternary ammonium group and a quaternary phosphonium group. In one or a plurality of embodiments, preferably the cationic polymer includes a constitutional unit derived from a monomer having a quaternary onium group. In one or a plurality of embodiments, preferably the cationic polymer is a polycationic polymer where a plurality of quaternary onium groups are included in one polymer molecule. For the molecular weight of the cationic polymer and the number of the quaternary groups included in the polymer, an optimal molecular weight and an optimal number can be selected suitably in accordance with the phoresis condition and the buffer solution composition.

In one or a plurality of embodiments, examples of the cationic polymer include polyquaternium and a dimethylamine-epichlorohydrin copolymer. In the present disclosure, "polyquaternium" refers to a cationic polymer including a constitutional unit derived from a monomer having a quaternary onium group. The polyquaternium can be confirmed in INCI (International Nomenclature for Cosmetic Ingredients) directory. In one or a plurality of embodiments, examples of polyquaternium include: polydiallyldimethylammonium salts such as polyquaternium-6 (poly(diallyldimethylammonium chloride), polyquaternium-7 (a copolymer of acrylamide and diallyldimethylammonium chloride), polyquaternium-4 (a diallyldimethylammonium chloride-hydroxyethyl cellulose copolymer), and polyquaternium-22 (a copolymer of acrylic acid and diallyldimethylammonium chloride); polyquaternium-1 (ethanol, 2,2', 2"-nitrilotris-, a polymer with 1,4-dichloro-2-butene and N,N,N',N'-tetramethyl-2-butene-1,4-diamine); polyquaternium-11 (a copolymer of vinylpyrrolidone and quaternized dimethylaminoethyl methacrylate); and polyquaternium-2 (poly[bis(2-chloroethyl)ether-alt-1,3-bis[3-(dimethylamino) propyl]ureal). In one or a plurality of embodiments, the dimethylamine-epichlorohydrin copolymer may include a constitutional unit other than the dimethylamine-epichlorohydrin, and for example it may include ethylene diamine and the like. From the viewpoint of availability, preferably the cationic polymer includes a polydiallyldimethylammonium salt and/or a dimethylamine-epichlorohydrin copolymer, and more preferably, it is composed of a polydiallyldimethylammonium salt and/or a dimethylamine-epichlorohydrin copolymer. In one or a plurality of embodiments, the cationic polymer is a chloride and/or a sulfide. The cationic polymer may be used alone, or in combination of two or more.

In one or a plurality of embodiments, the manufacturing method of the present disclosure includes joining resin substrates. As a result of this joining, a microchannel is formed. In one or a plurality of embodiments, joining the resin substrates is conducted by using surfaces on which a cationic polymer has been fixed and/or surfaces with which a cationic polymer solution has been brought into contact. In one or a plurality of embodiments, the joining process is conducted by pressing, heat-pressing, ultrasonic welding or the like. In one or a plurality of embodiments, the conditions for heat-pressing are: 40 to 200° C. or 60 to 120° C.; 1 to 100 kgf/cm$^2$ (0.0981 MPa to 9.81 MPa) or 5 to 50 kgf/cm$^2$ (0.4905 MPa to 4.905 MPa); and 1 second to 10 minutes or 10 seconds to 3 minutes.

In one or a plurality of embodiments, at least one of a pair of the resin substrates has a concavity formed on its surfaces to be joined. In one or a plurality of embodiments, such concavities may be formed on the surfaces to be joined of both the resin substrates. In one or a plurality of embodiments, the diameter of the circumscribed circle in the cross section of the concavity is 28 to 280 μm or 35 to 140 μm. In one or a plurality of embodiments, a through hole for introducing a sample and an electrophoresis running buffer is formed on the other resin substrate.

In one or a plurality of embodiments, examples of the resin include acrylic resins such as polymethylmethacrylate (PMMA), polymethyl methacrylate, polycarbonate, polyvinylidene chloride, cyclic polyolefin, polyether ether ketone, polystyrene, polytetrafluoroethylene (PTFE), cycloolefin, polypropylene, and polyethylene. From the viewpoint of its excellent optical transparency, polymethylmethacrylate is preferred.

[Microchannel Chip]

In one or a plurality of embodiments, the present disclosure relates to a chip comprising a microchannel. In one or a plurality of embodiments, the microchannel chip of the present disclosure is a chip manufactured by the manufacturing method of the present disclosure. In one or a plurality of embodiments, the chip of the present disclosure can provide an effect of separating with high accuracy respective fractions of hemoglobin in a short time. In one or a plurality of embodiments, the chip of the present disclosure can provide an effect of excellent reproducibility of an analysis.

In one or a plurality of embodiments, the chip of the present disclosure has a cationic polymer having a quaternary onium group, and the cationic polymer is fixed on the inner wall of a microchannel. Therefore, in one or a plurality of embodiments, the present disclosure relates to a chip having a microchannel formed by joining resin substrates, and a cationic polymer that has a quaternary onium group is fixed on the inner wall of the microchannel. In one or a plurality of embodiments, the cationic polymer is fixed to the microchannel via an anionic functional group. In one or a plurality of embodiments, the cationic polymer is fixed to the microchannel via an ionic bond. In one or a plurality of embodiments, the chip of the present disclosure has a cationic polymer having a quaternary onium group and fixed on parts to be joined of the resin substrates. In one or a plurality of embodiments, the chip of the present disclosure has resin substrates joined together via a cationic polymer having a quaternary onium group. The resin and the cationic polymer are as mentioned above.

In one or a plurality of embodiments, the chip of the present disclosure can be used for a specimen analysis. In one or a plurality of embodiments, the chip of the present disclosure can be used for an analysis such as an electrophoresis and a capillary electrophoresis. In one or a plurality of embodiments, the chip of the present disclosure can be used for analysis of a specimen derived from a living body. In one or a plurality of embodiments, an example of the specimen derived from a living body is a specimen including a blood component, and the examples include blood and blood derivatives, including components in blood. An example of the blood is blood collected from a living body. Examples of the blood derivatives including components in blood include whole blood, blood serum, blood plasma, and blood cells. Examples of the blood derivatives including a red blood cell component are separated or prepared from blood and include a red blood cell component, and the examples include a blood cell fraction from which blood plasma has been eliminated, a concentrate of blood cells, freeze-dried blood or blood cells, a hemolyzed sample prepared by subjecting whole blood to hemolysis, centrifuged blood, spontaneously-sediment blood, and washed blood cells. In one or a plurality of embodiments, examples of the analyte are proteins and the like, and in particular, hemoglobin, albumin and globulin are preferred. In one or a plurality of embodiments, examples of the hemoglobin include glycosylated hemoglobin, modified hemoglobin, and abnormal hemoglobin. In one or a plurality of embodiments, examples of the glycosylated hemoglobin include hemoglobin A1c, hemoglobin A1a, hemoglobin A1b, hemoglobin A1d1, hemoglobin A1d2, hemoglobin A1d3, and hemoglobin A1e. Examples of the abnormal hemoglobin include hemoglobin F, hemoglobin S, hemoglobin C, hemoglobin D, hemoglobin E, hemoglobin J, hemoglobin A2, and methemoglobin. In one or a plurality of embodiments, examples of the modified hemoglobin include carbamoylated hemoglobin, aldehyde hemoglobin, and acetylated hemoglobin. In one or a plurality of embodiments, an example of albumin is glycosylated albumin. In one or a plurality of embodiments, examples of the globulin include IgA, IgG, IgM, IgE, IgD, IgY, Fab, F (ab')$_2$, and antigen-antibody complexes formed by bonding these and an antigen. In one or a plurality of embodiments, an example of the globulin is globulin bonded to a marker. Examples of the marker include a dye, a fluorescent material, a luminescent material, a quantum dot, an enzyme, and nucleic acid.

In one or a plurality of embodiments, the chip of the present disclosure includes a microchannel, a concavity for retaining a sample, and a concavity for retaining an electrophoresis running buffer. The concavity for retaining a sample and the concavity for retaining an electrophoresis running buffer are in communication with each other through the microchannel. In one or a plurality of embodiments, the microchannel in the chip of the present disclosure is formed by joining two resin substrates.

In one or a plurality of embodiments, the channel in the chip of the present disclosure may be filled with an electrophoresis running buffer. Examples of the electrophoresis running buffer are as recited below.

Figure 1B:
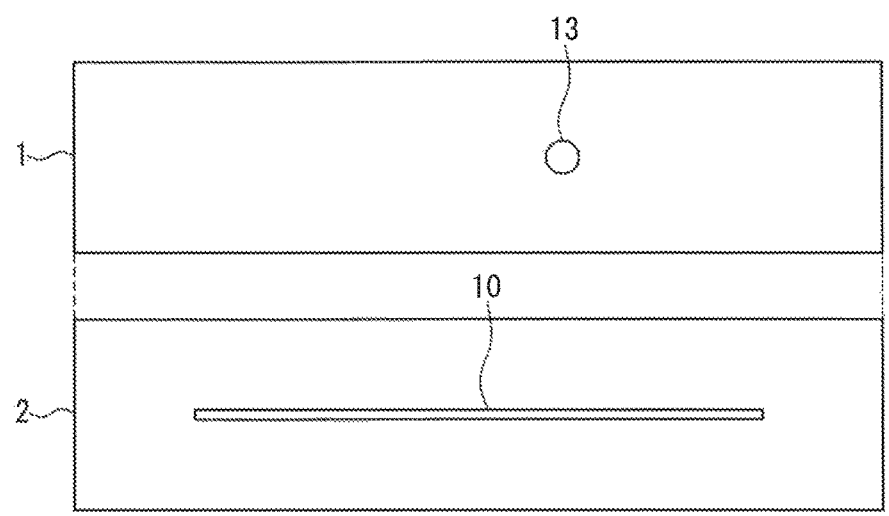
Figure 1C:
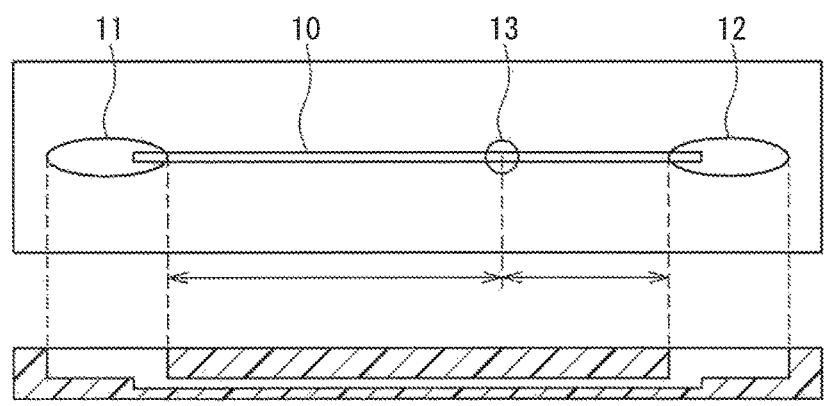

FIGS. 1A, 1B and 1C show a non-limiting embodiment of a chip of the present disclosure. FIGS. 1A, 1B and 1C are a schematic diagram for explaining the chip of the present disclosure. FIG. 1A is a top view of resin substrates 1, 2 FIG. 1B is a bottom view of the resin substrates 1, 2; and FIG. 1C is composed of an upper cross-sectional view and a side cross-sectional view of the chip. The chip shown in FIGS. 1A, 1B and 1C is formed of a pair of resin substrates 1, 2, and has a microchannel 10 formed in the interior. At the both ends of the microchannel 10, a sample reservoir 11 and an electrophoresis running buffer reservoir 12 are formed respectively. A detecting portion 13 is formed on the surface above the microchannel 10 between the sample reservoir 11 and the electrophoresis running buffer reservoir 12.

[Kit]

In one or a plurality of embodiments, the present disclosure relates to a kit for a specimen analysis, and the kit includes the chip of the present disclosure and a cartridge including a solution for analysis. In one or a plurality of embodiments, examples of the solution for analysis include an electrophoresis running buffer and a liquid for preparation of a sample.

For the electrophoresis running buffer, any conventionally known electrophoresis running buffers can be used. In one or a plurality of embodiments, the electrophoresis running buffer contains a pH buffer substance, a non-detergent amphoteric substance and water, and further contains an ionic pseudostationary phase and the like if necessary. In one or a plurality of embodiments, from the viewpoint of improving the accuracy of analysis and shortening the time for measurement, examples of the ionic pseudostationary phase include polysaccharides having anionic groups. Examples of the polysaccharides having anionic groups include sulfated polysaccharides, carboxylated polysaccharides, sulfonated polysaccharides, and phosphorylated polysaccharides. From the viewpoint of improving the accuracy of analysis and shortening the time for measurement, sulfated polysaccharides and carboxylated polysaccharides are preferred. In one or a plurality of embodiments, from the viewpoint of improving the accuracy of analysis and shortening the time for measurement, examples of the sulfated polysaccharides include chondroitin sulfate, heparin, heparan, fucoidan or the salts thereof. Among them, chondroitin sulfate or the salt thereof is preferred. Examples of the chondroitin sulfate include chondroitin sulfate A, chondroitin sulfate C, chondroitin sulfate D, and chondroitin sulfate E.

In one or a plurality of embodiments, the liquid for preparing a sample may have a composition similar to that of the electrophoresis running buffer. In one or a plurality of embodiments, the liquid for preparing a sample may have a composition different from that of the electrophoresis running buffer.

[Analysis Method]

In one or a plurality of embodiments, the present disclosure relates to a method for analyzing hemoglobin, and the analysis method includes measurement of an analyte in a sample by using the chip of the present disclosure. In one or a plurality of embodiments, according to the analysis method of the present disclosure, it is possible to improve the accuracy in measurement of the analyte in the sample, and preferably, it is possible to provide an effect of realizing improvement in the separation accuracy of the analyte and/or shortening of the time for measurement.

In one or a plurality of embodiments, the analysis can be conducted by separating the analyte in the sample by a separation analysis method. In one or a plurality of embodiments, an example of the separation analysis method is an electrophoresis, and in particular, a capillary electrophoresis is preferred.

In one or a plurality of embodiments, the analysis method of the present disclosure includes introducing a sample into an end of a microchannel of a chip and applying a voltage to the both ends of the microchannel. In one or a plurality of embodiments, the analysis method of the present disclosure includes diluting a specimen so as to prepare a sample, introducing an electrophoresis running buffer into an end of a microchannel of a chip and filling the microchannel with the electrophoresis running buffer, introducing the sample into the other end of the microchannel of the chip, and applying a voltage to the both ends of the microchannel. The electrophoresis running buffer is as mentioned above.

In one or a plurality of embodiments, preferably dilution of the specimen is conducted by using the above-mentioned liquid for preparing a sample.

The following explanation is about an example of a method for analyzing a sample by use of a capillary electrophoresis chip as shown in FIGS. 1A, 1B and 1C.

First, the electrophoresis running buffer reservoir 12 of the capillary electrophoresis chip is filled with an electrophoresis running buffer and the capillary channel 10 is filled with the electrophoresis running buffer by using a capillary action.

Next, the sample is placed in the sample reservoir 11 of the capillary electrophoresis chip having the capillary channel 10 filled with the electrophoresis running buffer.

The sample to be placed in the sample reservoir 11 can be prepared by diluting whole blood as a sample material. In one or a plurality of embodiments, the dilution ratio of the sample material is in the range of 1.2 to 200 times, and preferably in the range of 2 to 100 times or 3 to 80 times.

Then, a voltage is applied to the both ends of the capillary channel 10, namely, between the sample reservoir 11 and the electrophoresis running buffer reservoir 12. Thereby, the sample is introduced from the sample reservoir 11 to the capillary channel 10 and separated in the capillary channel 10, and thus, the sample including hemoglobin moves from the sample reservoir 11 to the electrophoresis running buffer reservoir 12. In one or a plurality of embodiments, the voltage to be applied to the both ends of the capillary channel 10 is in the range of 0.5 to 10 kV, and preferably 0.5 to 5 kV.

And a measurement is conducted at a predetermined position. In one or a plurality of embodiments, the measurement can be conducted by an optical process such as a measurement of absorbance. In a case where the analyte is hemoglobin, for example, it is preferable to conduct a measurement of absorbance at a wavelength of 415 nm.

The position for the measurement, namely, the length required for separation, can be determined suitably on the basis of the length of the capillary channel 10 or the like. For example, when the length of the capillary channel 10 is in the range of 10 to 150 mm, the position is distanced by the range of 5 to 140 mm, 10 to 100 mm or 15 to 50 mm from the end of the capillary channel 10 at the sample reservoir 11 side.

By conducting the analysis as mentioned above, it is possible to conduct a measurement of hemoglobin, and preferably it is possible to separate and measure HbA1c and any other hemoglobin component, and more preferably separate and measure a stable HbA1c that functions as an indicator in the diagnosis of diabetes and any other hemoglobin component. Examples of the other hemoglobin component include unstable HbA1c, HbA1d1, HbS, HbF, HbA2, and HbC. Furthermore, by analyzing the thus obtained electropherogram, it is possible to measure for example the rate of HbA1c (% HbA1c) and the amount of HbA1c. Therefore, the analysis method of the present disclosure can be utilized for the prevention, diagnosis, treatment and the like of diabetes.

The present disclosure can relate to one or a plurality of embodiments below.

[1] A method for manufacturing a chip comprising a microchannel, the method comprising:
fixing a cationic polymer having a quaternary onium group on at least one surface of each of a pair of resin substrates; and
joining the resin substrates together on the surfaces on which the cationic polymer has been fixed.

[2] A method for manufacturing a chip comprising a microchannel, the method comprising:
subjecting at least one surface of each of a pair of resin substrates to either a gas phase surface treatment or a liquid phase surface treatment;
bringing a cationic polymer solution having a quaternary onium group into contact with the treated surfaces; and
joining the resin substrates together on the surfaces that has been brought into contact with the cationic polymer solution.

[3] The manufacturing method according to [1], further comprising: introducing an anionic functional group into at least one surface of each of the resin substrates; and fixing the cationic polymer to the surface into which the anionic functional group has been introduced.

[4] The manufacturing method according to [3], wherein introduction of the anionic functional group is conducted by a gas phase surface treatment or a liquid phase surface treatment.

[5] The manufacturing method according to [2] or [4], wherein the gas phase surface treatment is selected from the group consisting of: a vacuum ultraviolet treatment, a plasma treatment, a corona discharge treatment, a flame treatment, and an ozone treatment.

[6] The manufacturing method according to any one of [1] to [5], wherein the quaternary onium group is selected from the group consisting of a quaternary ammonium group and a quaternary phosphonium group.

[7] The manufacturing method according to any one of [1] to [6], wherein the cationic polymer is selected from the group consisting of polyquaternium and a dimethylamine-epichlorohydrin copolymer.

[8] The manufacturing method according to any one of [1] to [7], wherein the cationic polymer comprises at least one selected from the group consisting of a polydiallyl dimethylammonium salt, a dimethylamine-epichlorohydrin copolymer, and a combination thereof.

[9] The manufacturing method according to any one of [1] to [7], wherein the cationic polymer is a polydiallyl dimethylammonium salt, a dimethylamine-epichlorohydrin copolymer, or a combination thereof.

[10] The manufacturing method according to any one of [1] to [9], wherein the cationic polymer is a chloride and/or a sulfide.

[11] The manufacturing method according to any one of [1] to [10], wherein the microchannel is formed by joining the resin substrates together.

[12] A chip comprising a microchannel, manufactured by the manufacturing method according to any one of [1] to [11].

[13] The chip according to [12], wherein the cationic polymer having a quaternary onium group is fixed to an inner wall of the channel.

[14] A chip having a microchannel formed by joining resin substrates, wherein a cationic polymer having a quaternary onium group is fixed to an inner wall of the microchannel.

[15] The chip according to [13] or [14], wherein the cationic polymer is selected from the group consisting of polyquaternium and a dimethylamine-epichlorohydrin copolymer.

[16] The chip according to any one of [12] to [15], which is used for a specimen analysis.

[17] A kit for a specimen analysis, comprising:
the chip according to any one of [12] to [16]; and
a cartridge comprising a solution for analysis.

[18] A method for analyzing hemoglobin, comprising a measurement of an analyte in a sample by using the chip according to any one of [12] to [16].

[19] The analyzing method according to [18], comprising:
diluting a specimen so as to prepare a sample;
introducing an electrophoresis running buffer into one end of the microchannel of the chip so as to fill the microchannel with the electrophoresis running buffer;
introducing the sample into the other end of the of the microchannel of the chip; and
applying a voltage to the both ends of the microchannel.

[20] The analyzing method according to [17], comprising:
filling the microchannel of the chip with an electrophoresis running buffer;
introducing a sample into the microchannel of the chip; and
applying a voltage to a whole or a part of the microchannel.

Hereinafter, the present disclosure will be described in detail by way of Examples and Comparative Examples. However, the present disclosure is not limited to the following examples.

EXAMPLES

Example 1

[Manufacture of the Chip]
A chip was manufactured by using parts as shown in FIGS. 1A, 1B and 1C.
<Preparation of Resin Parts>
For the material, PMMA (polymethylmethacrylate) was used, which was molded to make two resin parts, i.e., a resin part A (FIG. 1A) and a resin part B (FIG. 1B). A channel 10 was 0.04 mm×0.04 mm×30 mm, and the capacity of the sample reservoir 11 and the electrophoresis running buffer reservoir 12 each was 10 µL. Further, a detecting portion 13 is positioned so that its center would be distanced by 20 mm from the sample reservoir 11 and by 10 mm from the phoresis reservoir 12 respectively.
<Fixation of the Cationic Polymer>
The surfaces to be joined of the resin parts A and B were irradiated with ultraviolet rays by an excimer lamp under the atmospheric pressure so as to introduce an anionic functional group. Later the resin parts A and B were immersed in a treatment liquid 1 as mentioned below at room temperature for 24 hours.
(Treatment Liquid 1)
Polydiallyl dimethylammonium chloride (PDADMAC, polyquaternium-6, manufactured by Sigma-Aldrich Co.

LLC., molecular weight: 100,000 or less) 1% w/v, sodium hydroxide: 100 mM, aqueous solution After immersion, the resin parts A and B were washed sufficiently with water and air-dried by jetting compressed air. As a result of the serial processes, the cationic polymer was bonded to the anionic functional group on the surfaces to be joined of the resin parts and thus fixed to the surfaces.

<Formation of the Microchannel Chip>

The resin parts A and B each having a surface on which the cationic polymer had been fixed were heat-pressed in a state where the surfaces to be joined were in contact with each other (temperature: 80° C., pressure: 16 kgf/cm$^2$ (1.57 MPa), 1 minute), thereby obtaining the microchannel chip as shown in FIG. 1C. In this manner, a chip having the resin parts A and B joined to each other and having the cationic polymer fixed to the channel inner wall was obtained. Substantially no deformation was found in the microchannel of the obtained chip.

[Evaluation of the Joined Surface of the Chip]

Regarding the obtained chip, the joint between the resin part A and the resin part B was evaluated. The evaluation was based on the joining strength and leakage of liquid from the joined surfaces. The joining strength was checked by peeling forcefully the obtained chip on the joined surfaces and by measuring the depth of the peeling scar remaining on the joined surfaces. The leakage of liquid was checked by feeding a solution of dye to the capillary and observing microscopically. The result showed that the obtained chip had a joining depth of 2 μm or more, i.e., a sufficient joining strength was provided, while no leakage of liquid from the joined surfaces was observed. Namely, it was confirmed that the resin part A and the resin part B were joined sufficiently.

[Analysis of Hemoglobin]

The obtained chip was used for hemoglobin analysis by the capillary electrophoresis. An electrophoresis solution was prepared by adding the following substances to distilled water up to the concentrations below.

(Electrophoresis Solution 1

40 mM citric acid
1% w/v chondroitin sulfate C sodium
500 mM NDSB-201 (trade name of 3-(1-pyridinio)-1-propanesulfonate manufactured by Anatrave Products LLC)
0.1% w/v Emulgen LS-110 (trade name of polyoxyalkylene alkylether manufactured by KAO CORPORATION)
0.1% sodium azide
dimethylaminoethanol (pH regulator)
pH 6.0

(Electrophoresis Solution 2)

40 mM citric acid
1.25% w/v chondroitin sulfate C sodium
0.1% w/v Emulgen LS-110
0.1% sodium azide
dimethylaminoethanol (pH regulator)
pH 5.0

The capillary electrophoresis was conducted in the following manner.

1. A microchannel chip was set in an electrophoresis apparatus manufactured by ARKRAY, Inc.
2. The electrophoresis solution 2 (9 μL) was added to an electrophoresis running buffer reservoir of a microchannel chip, so that the microchannel was filled with the electrophoresis running buffer 2 by a capillary action.
3. Human whole blood was diluted 41 times with the electrophoresis solution 1, thereby preparing a sample.
4. The sample (9 μL) was added to a sample reservoir of the microchannel chip.
5. A positive electrode was brought into contact with the sample reservoir and a negative electrode was brought into contact with the electrophoresis running buffer reservoir, and a voltage of 1600 V was applied thereto so as to start electrophoresis.
6. Absorbance at 415 nm was measured at a detecting portion so as to obtain an electropherogram. The electrophoresis was conducted for 60 seconds.

Figure 2:
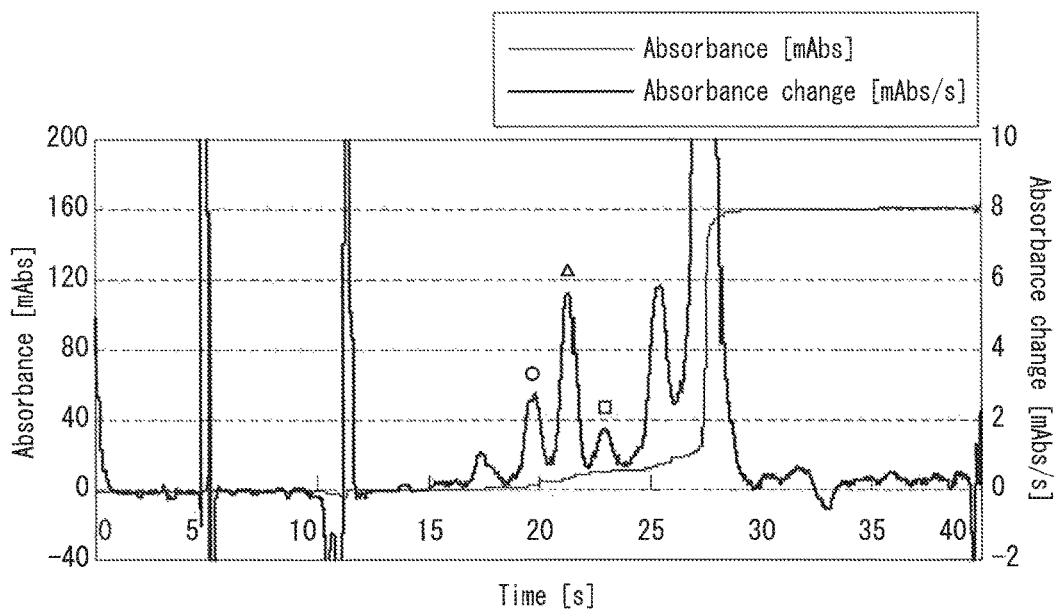
FIG. 2 is a graph showing an example of the result in Example 1.

The obtained analysis results are shown in FIG. 2. As shown in FIG. 2, the respective fractions of hemoglobin were detected within 30 seconds, and the respective fractions were separated sufficiently. Specifically, as shown in FIG. 2, the respective peaks of the unstable HbA1c (an open circle in FIG. 2), stable HbA1c (an open triangle in FIG. 2) and HbA1d1 (an open square in FIG. 2) were confirmed distinctly. Namely, it was confirmed that the chip in Example 1 can separate with high accuracy the respective fractions of hemoglobin in a short time.

Example 2

A microchannel chip was obtained similarly to Example 1 except that polystyrene was used for the material of the resin parts A and B and the temperature of heat-pressing was changed to 90° C. The obtained chip was used for evaluating the joined surfaces and analyzing hemoglobin similarly to Example 1. The obtained chip had sufficient joining strength and no leakage of liquid on the joined surfaces was found. There was also substantially no deformation in the microchannel of the obtained chip.

Figure 3:
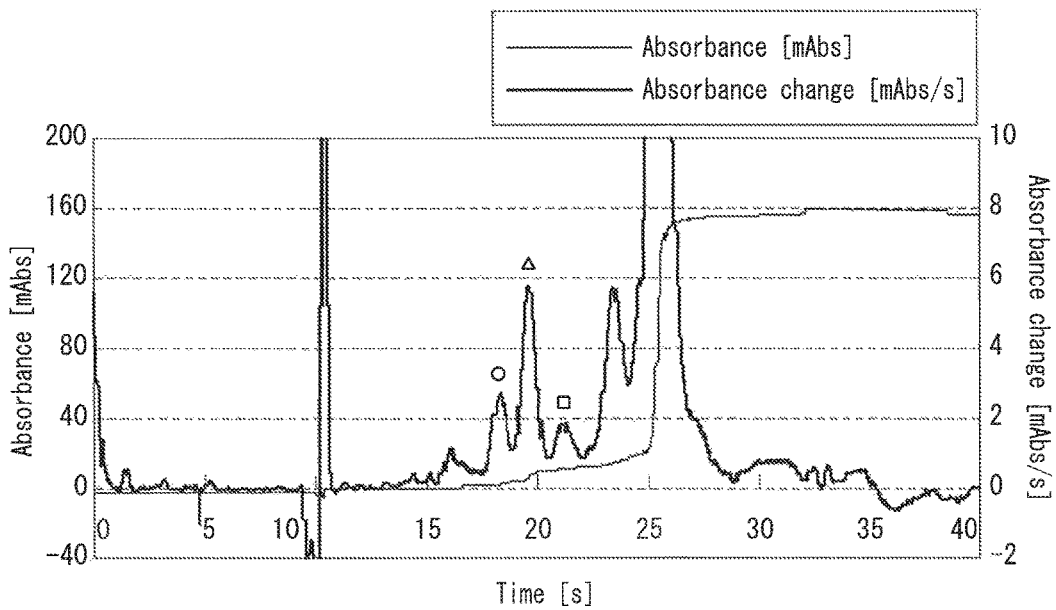
FIG. 3 is a graph showing an example of the result in Example 2.

The obtained analysis results are shown in FIG. 3. As shown in FIG. 3, the respective fractions of hemoglobin were detected within 30 seconds, and the respective peaks of the unstable HbA1c (an open circle in FIG. 3), stable HbA1c (an open triangle in FIG. 3) and HbA1d1 (an open square in FIG. 3) were confirmed distinctly. Namely, it was confirmed that the chip in Example 2 can separate with high accuracy the respective fractions of hemoglobin in a short time.

Example 3

A microchannel chip was obtained similarly to Example 1 except that cycloolefin was used for the material of the resin parts A and B and that the temperature of heat-pressing was changed to 90° C. The obtained chip was used for evaluating the joined surfaces and analyzing hemoglobin similarly to Example 1. The obtained chip had sufficient joining strength and no leakage of liquid on the joined surfaces was found. There was also substantially no deformation in the microchannel of the obtained chip.

Figure 4:
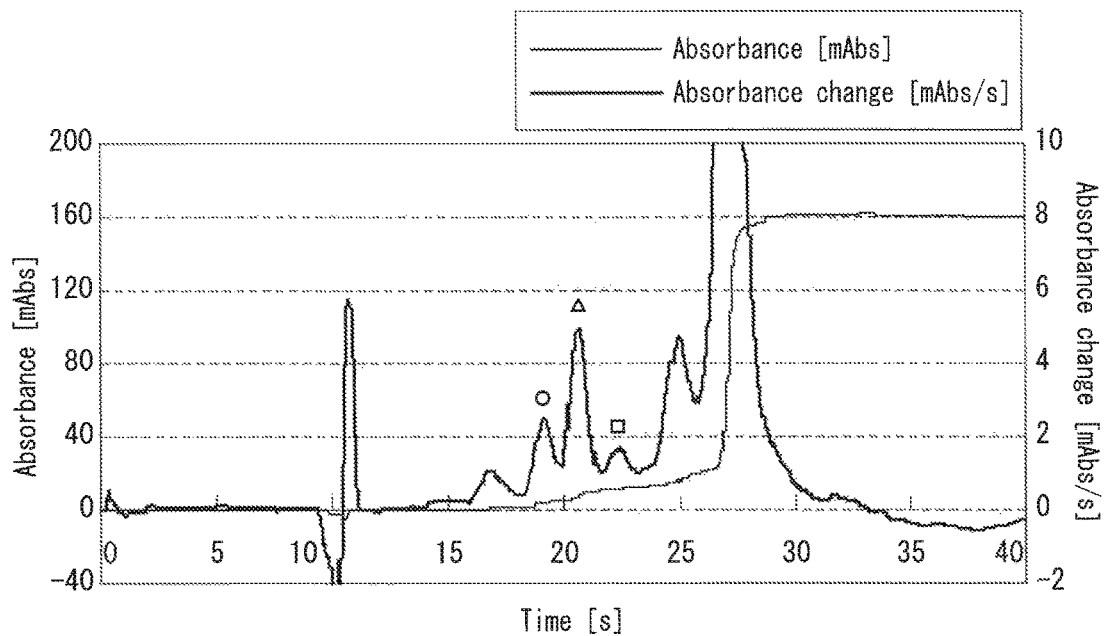
FIG. 4 is a graph showing an example of the result in Example 3.

The obtained analysis results are shown in FIG. 4. As shown in FIG. 4, the respective fractions of hemoglobin were detected within 30 seconds, and the respective peaks of the unstable HbA1c (an open circle in FIG. 4), stable HbA1c (an open triangle in FIG. 4) and HbA1d1 (an open square in FIG. 4) were confirmed distinctly. Namely, it was confirmed that the chip in Example 3 can separate with high accuracy the respective fractions of hemoglobin in a short time.

Example 4

A microchannel chip was obtained similarly to Example 1 except that the treatment liquid 1 was changed to a treatment liquid 2 as mentioned below.

(Treatment Liquid 2)

Poly[bis(2-chloroethyl)ether-alt-1,3-bis[3-(dimethylamino)propyl]urea], which is a quaternized substance (polyquaternium-2, CAS No. 68555-36-2, manufactured by Sigma-Aldrich Co. LLC.) 1% w/v, sodium hydroxide 100 mM, aqueous solution The obtained chip was used for evaluating the joined surfaces and analyzing hemoglobin similarly to Example 1. The obtained chip had sufficient joining strength and no leakage of liquid on the joined surfaces was found. There was also substantially no deformation in the microchannel of the obtained chip.

Figure 5:
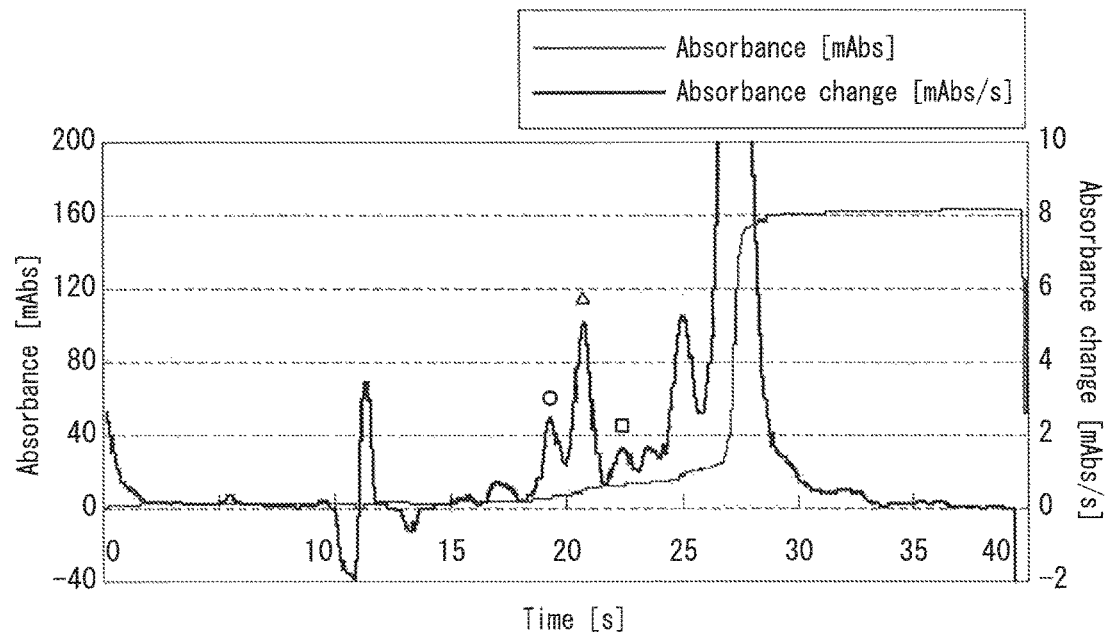
FIG. 5 is a graph showing an example of the result in Example 4.

The obtained analysis results are shown in FIG. 5. As shown in FIG. 5, the respective fractions of hemoglobin were detected within 30 seconds, and the respective peaks of the unstable HbA1c (an open circle in FIG. 5), stable HbA1c (an open triangle in FIG. 5) and HbA1d1 (an open square in FIG. 5) were confirmed distinctly. Namely, it was confirmed that the chip in Example 4 can separate with high accuracy the respective fractions of hemoglobin in a short time.

Example 5

A microchannel chip was obtained similarly to Example 1 except that the treatment liquid 1 was changed to a treatment liquid 3 as mentioned below.
(Treatment Liquid 3)
Dimethylamine-epichlorohydrin copolymer (trade name: UNISENCE™ KHE105L, manufactured by SENKA Corporation) 1% w/v, sodium hydroxide 100 mM, aqueous solution The obtained chip was used for evaluating the joined surfaces and analyzing hemoglobin similarly to Example 1. The obtained chip had sufficient joining strength and no leakage of liquid on the joined surfaces was found. There was also substantially no deformation in the microchannel of the obtained chip.

Figure 6:
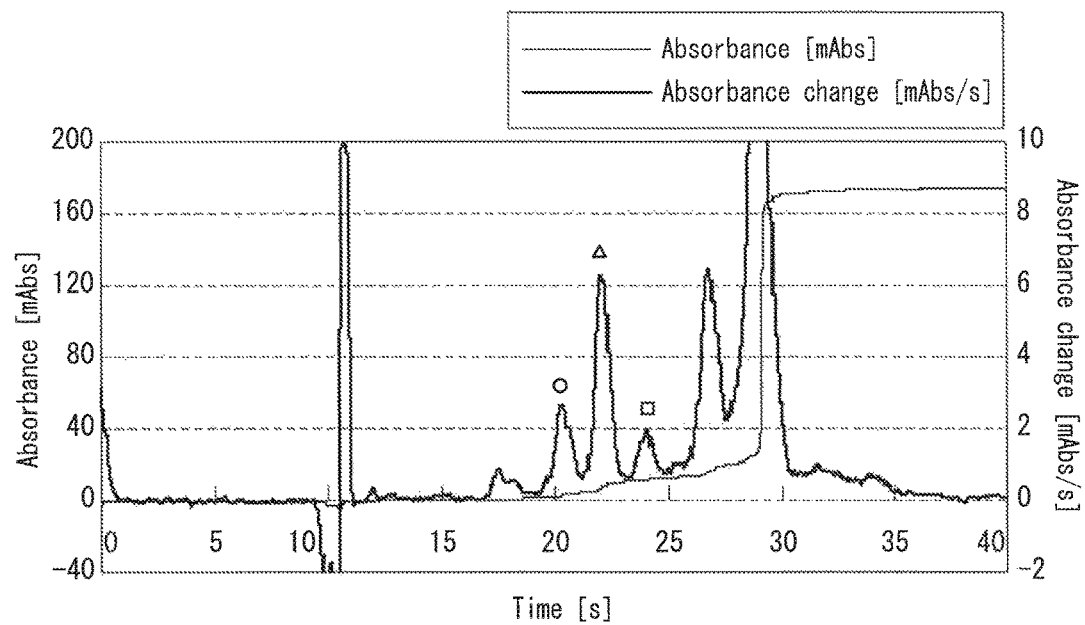
FIG. 6 is a graph showing an example of the result in Example 5.

The obtained analysis results are shown in FIG. 6. As shown in FIG. 6, the respective fractions of hemoglobin were detected within 30 seconds, and the respective peaks of the unstable HbA1c (an open circle in FIG. 6), stable HbA1c (an open triangle in FIG. 6) and HbA1d1 (an open square in FIG. 6) were confirmed distinctly. Namely, it was confirmed that the chip in Example 5 can separate with high accuracy the respective fractions of hemoglobin in a short time.

Comparative Example 1

Figure 7:
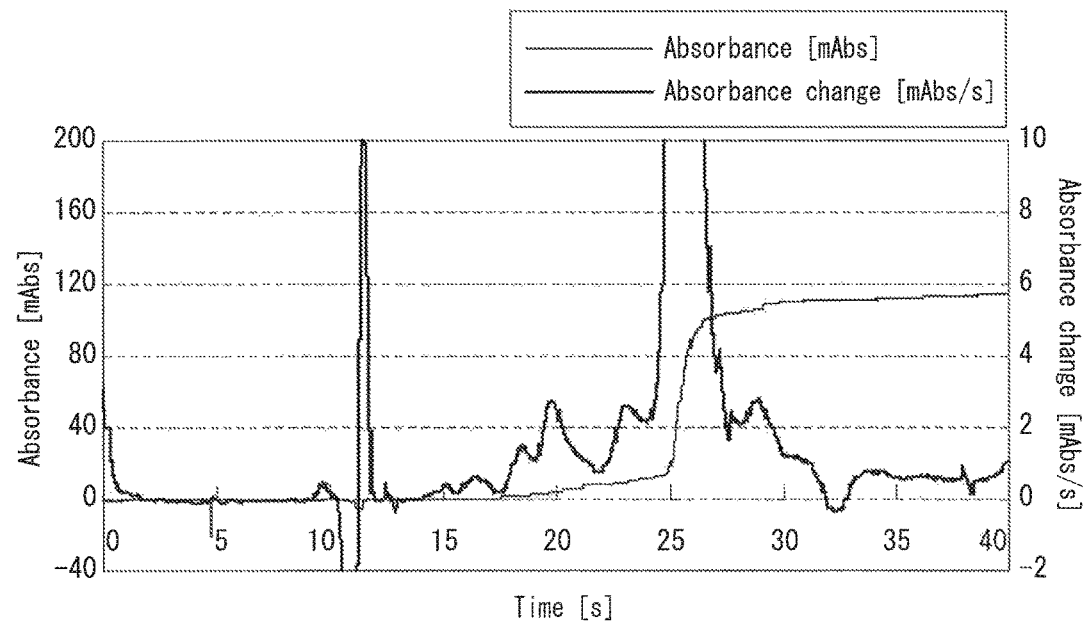
FIG. 7 is a graph showing an example of the result in Comparative Example 1.

A microchannel chip was obtained similarly Example 1 except that the treatment liquid 1 was changed to a treatment liquid 4 as mentioned below.
(Treatment Liquid 4)
Polyethyleneimine (PEI, manufactured by Waco Pure Chemical Industries Ltd.) 1% w/v, aqueous solution The obtained chip was used for evaluating the joined surfaces and analyzing hemoglobin similarly to Example 1. The obtained chip had sufficient joining strength and no leakage of liquid on the joined surfaces was found. The obtained analysis results are shown in FIG. 7. As shown in FIG. 7, the respective fractions of hemoglobin were detected within 30 seconds, but the respective peaks were not clear, and separation of the respective fractions of hemoglobin was insufficient.

Comparative Example 2

A microchannel chip was obtained similarly to Example 1 except that the treatment liquid 1 was changed to a treatment liquid 5 as mentioned below.

Figure 8:
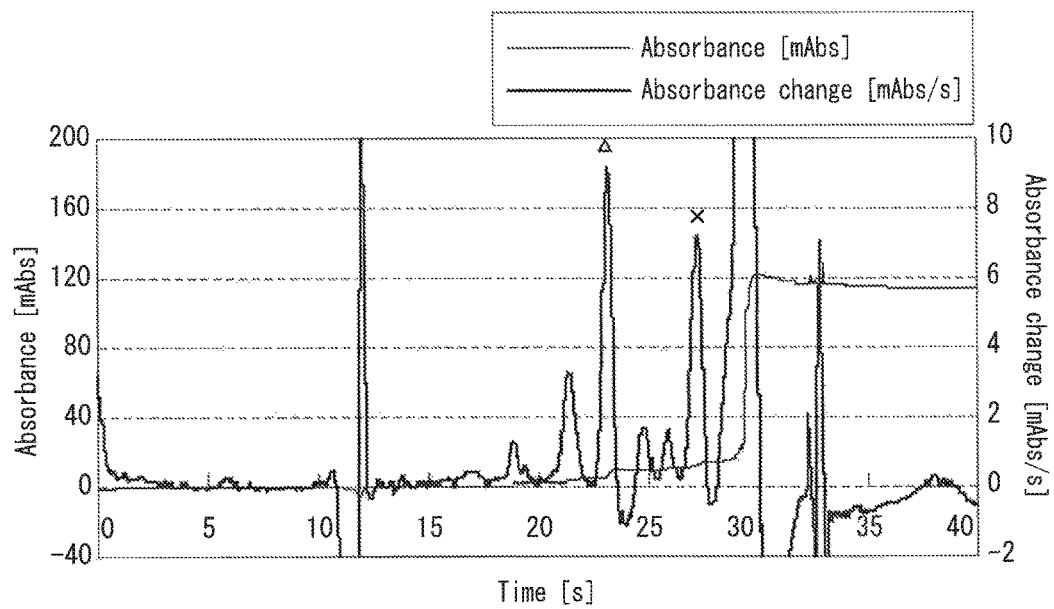
FIG. 8 is a graph showing an example of the result in Comparative Example 2.

(Treatment Liquid 5)
Polyallylamine hydrochloride (PAA, manufactured by NITTOBO MEDICAL CO., LTD.) 1% w/v, sodium hydroxide 100 mM, aqueous solution The obtained chip was used for evaluating the joined surfaces and analyzing hemoglobin similarly to Example 1. The obtained chip had sufficient joining strength and no leakage of liquid on the joined surfaces was found. The obtained analysis results are shown in FIG. 8. As shown in FIG. 8, the respective fractions of hemoglobin were detected within 30 seconds, but a problem occurred, i.e., the absorbance was degraded after detecting the stable HbA1c fraction (an open triangle in FIG. 8) and HbA0 fraction (a cross in FIG. 8).

Comparative Example 3

A microchannel chip was obtained by irradiating the resin parts A and B prepared in Example 1 with ultraviolet rays in order to introduce an anionic functional group and by applying aminosilane thereon as indicated below.
<Application of Aminosilane>
The surfaces to be joined of the resin parts A and B were irradiated with ultraviolet rays by use of an excimer lamp under the atmospheric pressure so as to introduce an anionic functional group into the surfaces. Later, the resin parts A and B were immersed in a treatment liquid 6 as mentioned below at 30° C. for 3 hours.
(Treatment Liquid 6)
Aminopropyltrimethoxysilane (KBM-903, manufactured by Shin-Etsu Chemical Co., Ltd.) 5% w/v, aqueous solution After the immersion, the resin parts A and B were washed sufficiently with water and air-dried by jetting compressed air.
<Formation of Microchannel Chip>
The resin parts A and B having surfaces joined and applied with the aminosilane were heat-pressed in a state being in contact with each other on the joined surfaces, thereby obtaining the microchannel chip as shown in FIG. 1C. The heat-pressing was conducted at a temperature of 70° C. and at a pressure of 18.7 kgf/cm$^2$ (1.83 MPa) for 5 minutes.

As a result of the serial processes, the aminosilane and the resin parts were covalently-bonded together, and the aminosilanes were covalently bonded together, thereby the resin parts were joined with each other and an aminosilane layer was formed on the inner wall of the capillary.

Figure 9:
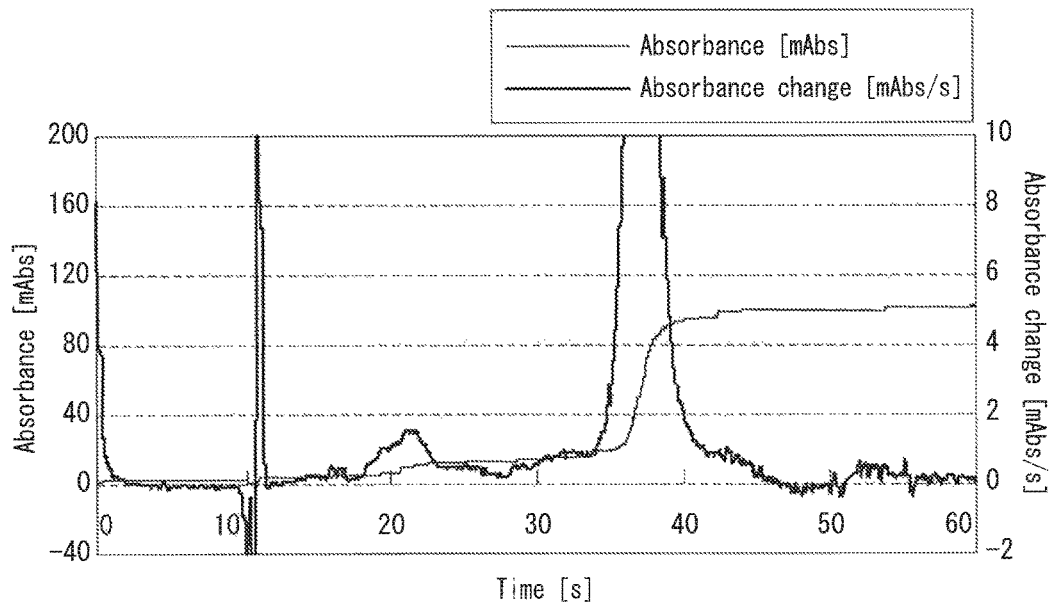
FIG. 9 is a graph showing an example of the result in Comparative Example 3.

The obtained chip was used for evaluating the joined surfaces and analyzing hemoglobin similarly to Example 1. The obtained chip had sufficient joining strength and no leakage of liquid on the joined surfaces was found. The obtained analysis results are shown in FIG. 9. As shown in FIG. 9, the respective fractions of hemoglobin were not detected within 30 seconds. Moreover, the peaks of the respective fractions were unclear, which indicates that separation of the respective fractions was insufficient.

[Reproducibility Test]

Daily rate reproducibility test was conducted by using the microchannel chips obtained in Examples 1, 4, 5 and Comparative Examples 1 and 2. In the reproducibility test, each of the chips was sealed tightly with a desiccant and preserved for 5 days under a condition of 50° C. The chip was measured respectively twice before preservation, two days after the preservation and five days after the preservation. The measurement was conducted just like the analysis of hemoglobin in Example 1, and the stable HbA1c value was calculated by the equation below. The results are shown in Table 1 below.

HbA1c (%)=('absorbance of HbA1c fraction'/'absorbance of total hemoglobin')×100

TABLE 1

|  | Before preservation | 2-days after | 5-days after | CV (%) |
|---|---|---|---|---|
| Example 1 | 5.3 | 5.3 | 5.2 | 1.04 |
|  | 5.3 | 5.2 | 5.2 |  |
| Example 4 | 5.2 | 5.3 | 5.3 | 0.98 |
|  | 5.2 | 5.3 | 5.3 |  |
| Example 5 | 5.3 | 5.2 | 5.3 | 0.77 |
|  | 5.3 | 5.3 | 5.3 |  |
| Comparative Example 1 | 5.5 | 5.7 | 5.7 | 4.35 |
|  | 5.7 | 5.4 | 5.1 |  |
| Comparative Example 2 | 5.3 | 5.7 | 5.4 | 5.20 |
|  | 5.8 | 6.0 | 6.0 |  |

As shown in Table 1, the CV (Coefficient of Variation) values indicating reproducibility were 4% or higher for the chips in Comparative Examples 1 and 2 while the same values were around 1% for the chips in Examples 1, 4 and 5. That is, it was found that the chips in Examples 1, 4 and 5 provide a favorable reproducibility.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An electrophoresis chip comprising:
    a first resin substrate and a second resin substrate; and
    a microchannel between the first and second resin substrates,
    wherein a surface of the first resin substrate and a surface of the second resin substrate face each other and a cationic polymer having a quaternary onium group is fixed on the facing surfaces of the first resin substrate and second resin substrate, and
    wherein the first and second resin substrates are joined together via the cationic polymer.

2. The electrophoresis chip according to claim 1, wherein the cationic polymer is selected from the group consisting of polyquaternium, a dimethylamine-epichlorohydrin copolymer, and a combination thereof.

3. A method for analyzing an analyte present in a biological specimen, the method comprising:
    introducing a sample from the biological specimen into the microchannel of the electrophoresis chip according to claim 1, where the microchannel contains an electrophoresis running buffer;
    applying a voltage to a whole or a part of the microchannel sufficient to separate the analyte for measurement; and
    measuring the analyte concentration in the specimen sample.

4. The method according to claim 3, wherein the analyte is selected from the group consisting of albumin, globulin and hemoglobin.

5. The method according to claim 4, wherein the analyte is hemoglobin.

6. A kit for a specimen analysis, comprising:
    the electrophoresis chip according to claim 1; and
    a cartridge comprising a solution of the specimen for analysis.

* * * * *